US005460966A

United States Patent [19]

Dixon

[11] Patent Number: 5,460,966

[45] Date of Patent: Oct. 24, 1995

[54] TREATMENT OF TEXTILES

[75] Inventor: Michael W. Dixon, Dallas, N.C.

[73] Assignee: Sandoz Ltd., Basel, Switzerland

[21] Appl. No.: 360,861

[22] Filed: Dec. 21, 1994

Related U.S. Application Data

[63] Continuation of Ser. No. 31,739, Mar. 15, 1993, abandoned.

[51] Int. Cl.[6] .............................. C07G 17/00; C12N 9/96; C12N 9/42; C09B 67/00

[52] U.S. Cl. .......................... 435/263; 435/267; 435/188; 435/209; 252/8.6; 8/401

[58] Field of Search .................................... 435/263, 267, 435/188, 209; 8/401, 524, 137; 252/174.12, 8.6, DIG. 12

[56] References Cited

U.S. PATENT DOCUMENTS

| | | | |
|---|---|---|---|
| 3,934,971 | 1/1976 | Blanchard et al. | 8/14 |
| 4,643,736 | 2/1987 | Cholley | 8/108.1 |
| 4,881,941 | 11/1989 | Dixon | 8/482 |
| 4,912,056 | 3/1990 | Olson | 435/263 |

FOREIGN PATENT DOCUMENTS

| | | | |
|---|---|---|---|
| 6460661 | 3/1989 | Japan | C09B 67/00 |

OTHER PUBLICATIONS

Kawaguchi et al. CA 119(4):29921n Chemical Abstracts.
Mori et al. CA 118(26): 256510a Chemical Abstracts.
Shimada et al. 910009600 JICST–Abstracts.
Pentel (JP 1060661) Abstract from Derwent 89–112305/15.

*Primary Examiner*—Michael G. Wityshyn
*Assistant Examiner*—T. J. Reardon
*Attorney, Agent, or Firm*—Robert S. Honor; Richard E. Vila; Andrew N. Parfomak

[57] ABSTRACT

A single bath process for imparting both a stonewashed and overdyed appearance to denim textiles and articles is disclosed. The single bath comprises a dye, a cellulase enzyme and optionally but preferably a salt.

14 Claims, No Drawings

TREATMENT OF TEXTILES

This is a continuation of application Ser. No. 08/031,739, filed Mar. 15, 1993, now abandoned.

BACKGROUND OF THE INVENTION

The present invention relates to the treatment of dyed textiles, and more particularly to providing denim textiles which have an overdyed and stone washed appearance.

DESCRIPTION OF THE PRIOR ART

Dyed cellulosic textiles which are commonly known as "denim" are used in making a large variety of products, especially garments such as so-called "blue" jeans, skirts, jackets, shirts, as well as other products such as bags, and purses. Denim textiles (or simply "denim") are generally constructed of a warp yarn which is woven with a filling yarn. Generally, the warp yarn is dyed a color such as indigo, blue, black or other color while the filling yarn is generally an unbleached or white yarn. Denim textiles where both the warp yarn and the filling yarn are dyed are also known.

One class of such products are garments and articles which are given a worn appearance, generally referred to as "stone washed". This class of products may be created by actually washing the denim in the presence of an abrasive substance such as pumice stones. Alternately, these products may also be created with the use of a process which utilizes treatment of the denim in a bath containing a cellulase enzyme. Combination treatments with both pumice stones and cellulase enxymes are also particularly effective. Desizing can proceed or accompany the abrading process. In cellulase treatments the denim garments and articles are contacted with a bath containing cellulase enzymes, and optionally stones, for a sufficient time so to impart the desired degree of a worn appearance and at process conditions which are dictated by the conditions at which the enzymes are active. Upon reaching a desired degree of stonewashed appearance, the cellulase enzymes are then typically deactivated or removed, such as by flushing the bath containing the enzymes and rinsing the treated denim.

A further class of denim containing products are garments and articles which may be characterized as "overdyed" denim. Such product may be produced by subjecting the dyed denim, particularly dyed denim having undyed fill yarn, to a further dyeing step. The further dyeing step imparts to the denim a particular color "tint" which is introduced by the dye, which is especially evident from the fill yarn. This further dyeing step acts to primarily dye the fill yarn of the desized denim but also impart some degree of dyeing to the previously dyed warp yarn. Producing overdyed denim garments and articles requires that the desized denim is contacted in an dye bath with a selected dye under appropriate conditions. For such dyeing operations, direct dyes as defined in the *Colour Index* are generally used. The denim containing products are garments and articles are contacted with the direct dye in a bath under conditions which are dictated by the direct dye selected. These conditions are generally at a temperature in the range of 190°–200° F., for a period of approximately ½ hour to 2½ hours in an aqueous bath which typically further includes an effective amount of a salt generally to provide a bath concentration of 5–40 g salt per liter of bath. Typical dye baths are in the pH range of 7 to 8½.

A third class of products combines the effects of both the "stone washed" and the "overdyed" characteristics, and is known as the "distressed" look. Such an effect is presently obtained only by a sequential process, wherein the denim garments and articles are typically first treated with abrasive materials and/or an effective amount of a cellulase enzyme to achieve a "stone washed" appearance, followed by a subsequent step wherein garments and articles are subsequently contacted with a suitable dye in a dye bath under appropriate process conditions so to achieve the desired overdyed effect. Due to their stone washed treatment the resultant products are more flexible as evidenced by a softer hand as compared to denim which has not been treated in a "stone washing" process. Due to the overdyeing of the denim, particularly the dyeing of the fill yarn as well as portions of the dyed warp yarn there is imparted a further desired coloring effect. Characteristically, the first process step of effecting a stonewashed appearance imparts an abraded or worn appearance to the denim textile and introduces variations in the color of the dyeing. The second process step of overdyeing the article introduces a second color to the textile which is most visibly apparent in the previously undyed fill yarn, and further at the abraded areas of the denim textile or article imparted in the prior stonewashing step. The resultant products are striking in appearance, frequently featuring subtle shading and hue variations within the denim itself.

The prior art methods for the overdyeing of abraded denim which constitute two step processes, namely sequential arrangement of a first stonewash process where the textile is pretreated to impart improved softness and color variation to desized denim, followed by a second step, that of overdyeing the textile. It should be apparent that the order of these process steps must be carefully followed as the initial stonewash process imparts color variations (such as variations in the depth of dyeing and hue) in the dyed warp yarn which are subsequently overdyed along with the undyed fill yarn in the subsequent overdyeing step. While the practice of such process steps provides for an effective method for the production of denim articles and garments imparted with overdyed and stonewashed characteristics, such processes require the control of plural process conditions within each of the two steps practiced.

DESCRIPTION OF THE INVENTION

The present invention provides a process for the treatment of denim textiles by conducting a cellulase treatment in the presence of a dye. The present invention further provides an aqueous textile treatment bath comprising at least one dye effective for the dyeing of cellulose containing textiles or articles, preferably denim, and at least one cellulose-active enzyme effective for imparting a distressed or stonewashed effect upon cellulose containing textiles or articles, preferably denim. The process according to the invention may be incorporated into conventional denim textile treatment process, particularly processes which are directed to treating denim textiles or goods to impart an overdyed and distressed (or stonewashed) appearance thereto.

The present invention also provides a textile treatment preparation comprising at least one dye effective for the dyeing of cellulose containing textiles or articles, preferably denim, and at least one cellulose-active enzyme effective for imparting a distressed or stonewashed effect upon cellulose containing textiles or articles, and optionally but preferably a salt. Other features of the invention will become more apparent from the following detailed description.

Cellulose-active enzymes, also known to the art as "cellulases" which are useful in the practice of the present invention include those cellulose-active enzyme containing compositions and preparations which are well known to the textile industry. A wide variety of such compositions are available and are suitable in the practice of the present invention. These preparations include compositions and finishing agents are known for use for imparting a stone-washed or distressed effect to textiles, especially denim, as well as those which are known to the textile industry for other applications such as finishing agents. Such useful cellulase enzyme preparations include those which are presently known and/or marketed in the textile arts and particularly include those preparations which are useful as finishing agents for cellulose containing textiles such as cotton textiles, as well as stonewashing assistants or agents useful for imparting a stonewashed effect upon denim textiles. Those suitable for use in the treatment of denim textiles and articles to impart a distressed or stonewashed appearance are preferred as being particularly suited to the practice of the invention. These cellulase active enzyme containing compositions and preparations may contain a mixture of cellulases as produced by a native source, such as a microorganism or alternately may contain one or more cellulase degrading enzymes which have been produced by recombinant technology. Typically, the cellulose-active enzyme containing compositions will use endo-cellulases or mixtures thereof which comprise at least about 50% endo-cellulases and other cellulose degrading cellulases including exo-cellulases. Other cellulase enzymes which act on cellulose enzymatic degradation products may be present as well, for example cellobiohydrolase and/or cellobiase.

Cellulase enzymes are well known to exhibit their action optimally or only under certain conditions of pH and temperature, as well as to be subject to deactivation in the presence of various elements or substances. In general, it is recognized that a given enzyme has a pH and temperature range over which its activity is optimum and a broader range of pH and temperature over which it exhibits activity, even though its activity at the limits of the broader range may be judged to be only a fraction, e.g., about 10% of its activity within the optimum ranges. For definition purposes herein, optimum activity is defined as a condition of pH and/or temperature which achieves at least 50% of the maximum activity which an enzyme can exhibit when assayed as a function of pH and temperature. An optimal activity pH range will be the pH range over which the enzyme exhibits such optimum activity independent of temperature. An optimal activity temperature range will be the temperature range over which the enzyme exhibits such optimum activity independent of pH. However, the optimal pH and temperature ranges for a particular enzyme do not necessarily result in optimal activity as such at all points within both ranges. For example, an enzyme may exhibit optimum activity at pH 5.5 at say, 60° C., but not at 70° C., even though optimum or even maximum activity may be exhibited at 70° C. at pH 4.5. Hence, optimum activity of an enzyme as such is a function of both pH and temperature. Beyond the limits of the broader or general ranges of activity, the enzymes are essentially inactive. In carrying out the invention process, the cellulase will be selected such that its general activity in terms of pH and temperature is found to provide satisfactory results with the particular dye selected for use.

The amount of cellulase enzyme employed will be largely dependent upon the desired length of the treatment, the treatment conditions and the ultimate effect sought. Expressed in units of cellulase activity, the amount of cellulase enzyme employed may vary over a wide range, such as from at little as 900 CMC units per pound of textile, up to about 6000 CMC units per pound of textile, or even more. Preferably amounts of from 1500 to 6000 CMC units per pound may generally be employed, and amounts of from about 2000 to about 3500 units per pound may be employed over the more typical treatment periods, for example 35–50 minutes so obtain goods results with considerably reduced white streaking and good final product quality.

Generally, for most desired treatments, the amount of cellulase enzyme employed will be within the range which is conventionally used to abrade textiles under the pH, time and temperature conditions which are normally associated with the cellulase enzyme absent the dye. One typical treatment conditions includes the presence of cellulase enzyme in the range of about 2000–3000 CMC units per pound of textile, over a treatment period of 15–60 minutes. Suitable treatment temperature is a temperature range wherein the cellulase enzyme is sufficiently active so to impart the stonewashed effect, which is recognized as dependent upon the particular cellulase enzyme utilized. Conventionally, a temperature of between about 130° and about 140° F. is effective.

The dyes which find use are water soluble or water-dispersible dyes which are useful in dyeing cellulose auch as direct dyes and fiber reactive dyes. Preferably the dyes are direct dyes. Useful to the invention are the direct dyes which are well known to the art and include those which are defined in the *Colour Index,* Volume 2, pp. 2005–2478 (The Society of Dyers and Colourists, London, 1971) the contents of which are herein incorporated by reference. Most of the direct dyes belong to the dis-, tris- and polyazo classes, while the minority of direct dyes are categorized in the monoazo, stilbene, oxazine, thiazine and phthalocyanine categories. Usually, the direct dyes are anionic in character relative to cellulose and are applied from an aqueous bath containing an electrolyte. Such an electrolyte is generally formed by the addition to the dye bath with at least an effective amount of a salt generally used in conjunction with a direct dye. Most frequently the salt is sodium chloride, sodium sulfate or sodium sulfate decahydrate (Glauber's salt).

In accordance with the inventive teaching there is provided a process for the treatment of denim textiles or articles containing denim textiles to simultaneously impart a stone-washed and overdyed appearance thereto. The process is advantageously carried out on dyed denim textiles as well as on articles containing or made from such dyed denim textiles. The denim textiles may be in unsewn condition or sewn partially or in fully finished product condition. Denim textiles which are composed of less than 100% cellulose fibers, such as in the case of fiber blends which include both cellulosic and non-cellulosic fibers may be treated. Such fibers may be incorporated in the fill yarn or the dyed warp yarn or both. An example of such a denim textile containing less than 100% cellulose fibers are so called "stretch" blends which may be blends which comprise 65% cotton and 35% of a synthetic polyester fibers. The process is advantageously practiced with dyed denim articles of apparel in otherwise finished product form. Particularly contemplated as such articles of apparel are pants, jeans, skirts, shirts and jackets.

According to the inventive process, the denim textiles are contacted in a single aqueous bath which comprises effective amounts of a cellulase enzyme, a direct dye, and a salt under process conditions which allow for the action of both the cellulase enzyme and the direct dye to both degrade and overdye the denim textile.

In accordance with the process of the present invention, the denim textiles are preferably first desized. Desizing of the denim textile may be according to conventional techniques including contacting the denim textiles with one or more baths containing desizing agents, such as conventional desizing agents or an effective amount of an amylase enzyme.

The relative proportions of the constituents used in accordance with the single bath process taught herein are to be understood as variable over a wide range and are in great part dependent upon the ultimate textile treatment to be effectuated. Variables to be considered include process conditions such as time, temperature, concentration, as well as other conditions which may be dependent upon the process and/or apparatus which are to be utilized. Further variables effecting the amount of constituents include considerations related to the particular constituents selected, such as the particular cellulase enzyme preparation and direct dye selected. Other considerations dependent upon the desired final product include the ultimate degree or depth of dyeing which is desired, and the ultimate degree of textile softening or stonewashing effect which is to be imparted to the textile by the treatment process. These relative proportions may be determined by routine experimental evaluation. By way of non-limiting example, various exemplary process conditions as well as single bath compositions are provided in the Examples described in detail below.

The single bath may also include further constituents which are conventional to the textile treatment arts. By way of example, but not by way of limitation, these include wetting agents, suspension agents, dispersants, surfactants, leveling agents, buffering agents and the like. One or more of these additives may be added to the single baths according to the invention in any amount which is not found to undesirably limit the operation of the cellulase and the direct dye.

The single bath may contain an acid and/or a buffer to establish or regulate the pH of the single bath so to be within the effective operating pH of the particular cellulase enzyme selected. The single bath may be formed by the addition of the direct dye and the salt to the water, after which a sufficient amount of an acid is added to the single bath so to adjust the pH to be within the effective operating pH of the cellulase enzyme. Afterwards, the particular cellulase enzyme is then added to the single bath. Subsequently a buffer may be added to the single bath in a sufficient amount to regulate the pH to be substantially in the pH range where in the cellulase enzyme exhibits its optimal activity. For these purposes, useful acids include inorganic or organic acids. Particularly contemplated as useful acids are organic acids such as acetic, citric and oxalic acids. As useful buffering agents come into contemplation conventional buffering agents including monosodium buffering agents such as sodium acetate, sodium carbonate, sodium phosphate and sodium hydroxide containing buffering agents. Typically effective amounts range from 1 to 6 grams per liter of the single bath water. These amounts are more preferably in the range of from 2 to 4 grams per liter of water.

A useful further constituent which may be included in the single bath is a surfactant. Such surfactants desirably exhibit a good detergent action, and may be of the non-ionic, amphoteric and/or anionic type. Preferably the surfactants are of the non-ionic or involve mixtures of non-ionic types with a minor portion, up to 30% of an amphoteric or anionic type. The surfactants facilitate the treatment and is also effective to complete the substantial desizing of the fabric, such as starch or other desizing agents. The amount of surfactant will typically range from about 0.5 to 5.0 grams per liter of bath water, preferably from 0.5 to 1.5 grams per liter of water.

In the single bath processes according to the invention that the concentration of the salt may be varied to increase the effectiveness of the dyes being used, so to increase the percentage of dye exhaustion onto the textile. In comparisons of single baths according to the invention containing a direct dye (Pyrazol® Fast Turquoise FBL) (available from Sandoz Chemical Inc., Charlotte, N.C.) at a pH of 4.5, and a temperature of 140° F., increasing the salt concentration from 10 grams per liter of bath liquid to 20 grams per liter of bath liquid was observed to improve the dye exhaustion from 84% to 90%. From this observation, it may be hypothesized that the present process may include salt concentrations in excess of those which would normally be expected as useful or particularly recommended for use with the particular direct dye selected.

Following treatment in the single bath taught herein, the denim textile may be rinsed as desired. The rinses may be hot, or cold water rinses and are generally a plurality of rinses. One or more of the rinses may also include a scavenger for dye components which may have been freed or remain as residual products from the single bath process. Such products include those conventionally known and used for such a purpose, such as those which are based on or include acrylate copolymers. One such known product is Sandopure® RSK which is presently commercially available from Sandoz Chemical Inc., Charlotte, N.C. Such products may be used in conjunction with an alkali such as soda ash, and each are typically used in amounts of up to about 3% by weight based on the dry weight of the goods being treated.

Following treatment in the single bath taught herein, the denim textile may be subjected to further conventional treatment steps. Such conventional treatment steps by way of example include finishing steps, such as treatment with softening, finishing, lubricating agents.

In one embodiment of the invention, there is provided a textile treatment preparation which includes at least a cellulase and a direct dye, and optionally but preferably at least one salt in an effective amount to form a electrolyte. Such a textile treatment preparation is a concentrate which is useful in the later formation of an aqueous treatment single bath. The said cellulase is preferably a cellulase containing preparation especially a cellulase containing preparation of the type which are presently commercially available. As noted above such commercially available cellulase containing preparations include those which are known useful to the textile arts for one or more purposes including stonewashing assistants and finishing agents. The said direct dye is preferably one or more direct dyes as may be described by the *Colour Index*. As an optional constituent but preferred for inclusion in the textile treatment preparation is the salt which useful in conjunction with the direct dye of the composition. The textile treatment preparations, (i.e., concentrates,) may be produced by the simple addition of two or more of the constituents together by any effective means for producing mixtures. For example, where the cellulase enzyme preparation, the direct dye, the salt and any further optional constituents are in the form of normally dry solids, measured amounts of the respective constituents may be introduced to a mixing means, such as a powder mixer, mill or tumbler which are then operated for a sufficient period to ensure thorough blending of the respective constituents. In a further example, where one or more of the essential and optional constituents are in the form of a liquid or semi-solid (paste, gel, etc.), it is preferred to independently mix the normally dry solid constituents to form a dry premixture, and then the liquid or semi-solid constituents together to form a liquid premixture. Subsequently the dry premixture and the liquid premixture may be combined and mixed by any effective means to ensure thorough mixing of the constituents forming the textile treatment preparation. For example, the mixing of the dry premixture and the liquid premixture may be by the use of a mixing vessel equipped with an agitator such as a mechanical paddle or magnetic stirring rod.

The textile treatment compositions may further comprise optional constituents including but not limited to those which have been discussed above, namely: wetting agents, suspension agents, dispersants, surfactants, leveling agents, buffering agents as well as further conventional constituents not particularly elucidated here. One or more of these additives may be added to the textile treatment compositions according to the invention in any amount which is not found to undesirably limit the operation of the cellulase and the direct dye.

Preferred forms of the textile treatment compositions are those wherein the constituents included are in a normally dry solid form. Dry forms of cellulase enzyme preparations are known.

A further preferred form of the textile treatment composition is one wherein the constituents may be in normally solid, liquid or semi-solid state but wherein the cellulase enzyme selected exhibits activity, preferably exhibits its optimum activity at a pH or pH range which encompasses the pH or pH range of the direct dye. Such textile treatment compositions are expected to exhibit good long term storage stability. It is also expected that textile treatment compositions having one or more non dry solid constituents wherein the difference between the pH or pH range at which the cellulase enzyme selected exhibits activity, preferably exhibits its optimum activity, and the pH or pH range of the direct dye is minimized will also exhibit good storage stability.

It is to be further understood that where the preferred textile treatment compositions include optional constituents, it is preferred that such constituents be present in normally dry solid form, or be present in such amounts, or that such optional constituents have a pH or pH range, such that the overall pH of the textile treatment composition be within the active pH of the cellulase enzyme incorporated therein.

The single bath process according to the invention may be carried out in any apparatus or process which may be used for effecting enzymatic treatment of denim textiles or garments and/or articles thereof. One form of useful apparatus are commercial type washing machines which are known for use in one-bath or two-bath processes. Typically the aqueous textile treatment bath will occupy about one-half of the capacity of the machine. The goods to be treated, namely the denim textile, garments and/or articles to be treated may be added at the beginning of the treatment process and are usually present in the machine in a quantity so to result in a weight ratio of goods to treatment bath which may range from 1:4 to 1:30, although the range of from 1:10 to 1:20 is more common. If pumice stones or other abrasive materials are to be added to enhance the abrasion of the denim textile they are usually added at this time. The pumice stones or other abrasive materials are typically added to provide a weight ratio of pumice stones or other abrasive materials to water in the general range of 0.5:1 to 1:4. More typically, this range is from 1:1 to 1:3.

Subsequent to a desizing process step, (although not necessarily immediately subsequent), the water is provided to the washing machine as a metered amount of both "hot" water (approximately 140° F.) from a domestic or commercial hot water supply and "cold" water (approximately 35°–80° F.). If the temperature is insufficient, the temperature may be raised to a suitable temperature by appropriate heating means, such as a heating element which is conventionally provided as part of the washing machine. Once an appropriate temperature is attained, requisite amounts of the cellulase enzyme preparation, direct dye and salt according to the invention, as well as further optional constituents, are then added the water to form the single bath according to the invention. Upon this addition, the treatment of the goods begins.

Other sequences for the addition of the compositions according to the invention are contemplated to be within the scope of the invention, such as the addition of less than all of the constituents making up a composition at one time, and the subsequent addition of less than all of the remaining constituents or all of the remaining constituents at a later time. Such a sequential addition of the composition may be desirable under certain circumstances, such as may be contemplated when the cellulase enzyme and other optional constituents (such as buffering agents) but not the dye is added to the bath so to permit pretreatment of the goods prior so to impart a stonewashing effect and only subsequently adding the dye and other remaining optional constituents to the single bath so begin the overdyeing of the goods at a later point in time. In any case, the dyeing is conducted in the presence of the cellulase.

A further sequence for the carrying out the single bath process contemplates the addition of the requisite amounts of the cellulase enzyme preparation, direct dye and salt according to the invention, as well as further optional constituents and then at a later time but prior to the conclusion of the treatment process adding a further amount of an acid or base so to adjust the pH level of the bath so to increase the activity of the direct dye and optionally deactivate the cellulase enzyme present. In a further alternative sequence, an additional amount of salt is added prior to the conclusion of the treatment process to increase the activity of the direct dye. In a still further alternative sequence, the temperature of the single bath is raised from an inital single bath temperature to a higher temperature during the process, i.e., increasing the temperature to a temperature above that at which the cellulase enzyme exhibits its optimal activity, or increasing the temperature to a temperature which is observed to increase the exhaustion of the dye, especially a direct dye.

Subsequent to the treatment process, the liquid is removed from the goods, and the goods are preferably rinsed with one or more rinses. The single bath treatment process may be followed by further conventional treatment process steps such as by further washing, rinsing, or finishing process steps.

In one such rinsing process the goods are rinsed in two stages, first by rinsing with water at the temperature of the water used in the prior process and dumping the water, and afterwards, by rinsing with water at a temperature which is at a sufficiently low temperature so to remove any remaining cellulase enzymes which are entrained in the goods.

An important aspect of the invention is in the provision of simultaneous treatment to provide a worn appearance and overdyeing in a single-bath. Surprisingly, the present inventors have found that this is achieved at temperatures which have not been known to the art to be particularly effective for the dye used. In the case of the use of a conventional direct dye which normally has a dyeing temperature in the range of 190°–200° F., the use of the cellulase enzyme as a dyeing assistant to the dye has been found to lower the effective dyeing temperature. The inventor has found that such direct dyes which had heretofore been known to be most effective at temperatures of approximately 190° F. and higher, are now found to be comparably effective at lower temperatures in the presence of the cellulase enzyme, at temperatures at which the cellulase enzyme is active. This depression in the effective dyeing temperature is typically in a range which 30°–50° F. lower than that which is recommended for the particular direct dye used. Therefore, it is now possible to practice a single-bath process where both desired effects of stonewashing and overdyeing are obtained. The practice of such a single-bath process provides numerous technical advantages including reduced process time due to the simultaneous working of both the enzyme and the direct dye; decrease in overall energy requirement which are realized by the effective depression in the temperature at which the direct dye is found to work, as well as time and material requirement savings.

The inventor has observed that the goods treated in accordance with the present inventive teaching exhibit level dyeing of the goods as is observed in the overdyed fill yarns as well as good exhaustion of the direct dye which is used. Further, an increase in the salt content has been observed to increase the dye exhaustion. Improvement in the dye exhaustion reduces the quantity of dye which must be ultimately disposed of and is a technical benefit which is important in view of environmental and product waste disposal considerations.

The foregoing invention will be more apparent by reference to specific embodiments which are representative of the invention. It is nonetheless to be understood that the particular embodiments described herein are provided for the purpose of illustration, and not be means of limitation, and that it is to be further understood that the present invention may be practiced in a manner which is not exemplified herein without departing from its scope.

EXAMPLES

Example A

To a front loading Unimac® 30 washing machine were provided 1.7 lbs of a denim textile in the form of dyed blue jeans and 1.7 lbs of a denim textile in the form of textile swatches. The denim textile was dyed on the warp yarns with conventional indigo and sulfur dyes, and the fill yarns were undyed. To effectuate desizing of the denim, to the machine was added 28 liters of water at approximately 100° F., to which was added 0.017 lbs (or, 1% by weight based on the dry denim textile) of Sandoclean® PCA, a conventional non-ionic detergent composition (available from Sandoz Chemical Inc., Charlotte, N.C.), and 0.034 lbs (or, 2% by weight based on the dry denim textile) of technical grade soda ash. The goods:liquor ratio was 1:18. The temperature of the water in the machine was raised to 140° F. by operating the integrated heating element of the machine and then the agitator of the machine was energized to operate at a "slow" setting for a period of 10 minutes. At the slow setting the agitator operated for 3 seconds and then paused for 12 seconds, each time reversing the direction of rotation of the agitator. The rotational speed of the agitator was 30 rpm. Subsequently, for a further 5 minute period the machine was operated at a "wash" setting wherein the agitator operated for 12 seconds and then paused for 3 seconds, each time reversing the direction of rotation of the agitator. The rotational speed of the agitator was 30 rpm. Afterwards the liquid contents of the machine were removed. The contents of the machine were then subjected to two successive rinsing operations where 28 liters of water at 100° F. were provided to the machine, the machine was operated on the wash setting for 3 minutes after which the liquid contents of the machine were removed. At this time any sizing agent present in the goods is substantially removed.

The single bath process according to the invention was formed by adding 28 liters of water to the machine at 100° F., and subsequently raising and controlling the temperature of the bath by means of the integrated heating element to a temperature in the range of 135°–138° F. To the water was added 7 grams (0.25 grams/liter of bath) of a conventional non-ionic detergent which acts as a wetting agent and 14 grams (0.5 grams/liter of bath) of 56% acetic acid to adjust the pH to 4.5–5.5. Subsequently was added cellulase enzymes commercially available as "BACTOSOL® CA" (a cellulase enzyme containing preparation that hydrolyses cellulose to produce glucose and glucose polymers, available from Sandoz Chemical Inc., Charlotte, N.C.) which was indicated by the manufacturer to be optimally active at a temperature of approximately 130°–150° F., at a pH in the range of 3.8–5.5. Present in the machine was a cellulase enzyme concentration of 2940 CMC units per lb. of denim. Afterwards was added 560 grams (20 grams/liter of bath) of Glauber's salt and 1% by weight (based on the dry denim textile) of a direct dye solution Lumicrease® Orange 3LG (Colour Index Direct Orange 107) (available from Sandoz Chemical Inc.) which was prepared from a dry form according to the manufacturer's instructions. The machine was operated at the "wash" setting for 45 minutes, after which the liquid was removed from the machine. The treated denim was observed to have been effectively overdyed. It was also observed that good exhaustion of the dye was achieved by visual inspection of a sample of the liquid as it was removed from the machine.

Following the single bath treatment process, to the machine was added 28 liters of water at 100° F. and the machine was operated at the "wash" setting for 3 minutes so to rinse the textile, after which the liquid was removed from the machine.

After rinsing, 28 liters of water at 100° F. were added to the machine to which was then added 1% of a conventional polyacrylate containing dirt/dye suspension agent, Sandopure® RSK (available from Sandoz Chemical Inc., Charlotte, N.C.). The temperature was then raised to 140° F. by means of the integral heating element, and the machine was operated at the "wash" setting for 5 minutes. The liquid contents of the machine were then removed. Subsequently the denim textile was again rinsed by adding 28 liters of water at 100° F. and operating the machine at the "wash" setting for 3 minutes so to rinse the textile, after which the liquid was removed from the machine.

Next, the denim textile was treated in accordance with a conventional finishing process. To the machine was added 28 liters of water at 100° F. and 0.017 lbs 1% by weight (based on the dry denim textile) of Ceranine® HCA (available from Sandoz Chemical Inc.) a conventional cationic finishing agent used to impart lubricative, antistatic and softening properties to the textile. The machine was run on the "wash" setting for 5 minutes at a water temperature of 100° F. after which the liquid was removed from the machine.

The denim textile, i.e., "blue jeans" were extracted from the machine and dried in a conventional residential clothes dryer after which the blue jeans were removed and inspected. The denim textile was observed to be uniformly overdyed, providing a color cast to the previously dyed warp yarn and further with good coloration by the direct dye evident at abrasion points, seams, and in the fill yarn. The goods have been imparted with both a stonewashed effect and are overdyed in the single bath process.

The actual strength of dyeing was determined by establishing the dye exhaustion in accordance with the following test.

Dye Exhaustion

Two 20 gram pieces of bleached white cotton textile are provided.

To a first 500 ml laboratory beaker was provided one piece of textile, to which is added 495 ml of water at 190° F., 5 grams (10 grams/liter of water) of Glauber's salt, and 1% by weight (based on the dry denim textile) of a direct dye solution Lumicrease® Orange 3LG (Colour Index Direct Orange 107) which had been prepared according to the manufacturer's directions. The contents of the beaker were automatically stirred for 45 minutes on an apparatus which continually rotated the beaker at a speed of 60 rpm. Afterwards the textile was removed, and it was visually observed that all of the dye in the beaker had been exhausted and deposited upon the textile. The piece of textile was labeled as the "color control" and assigned a value of 100%, representative of complete dye takeup by the textile and exhaustion of the dye in the bath.

To a second 500 ml laboratory beaker was provided the other piece of cotton textile, to which is added 494 ml of water at 140° F., 5 grams (10 grams/liter of water) of Glauber's salt, sufficient acetic acid (58%, technical grade) 0.5 grams of "BACTOSOL® CA" (a cellulase enzyme containing preparation available from Sandoz Chemical Inc., Charlotte, N.C.) (1 gram per liter of water) and 1% by weight (based on the dry denim textile) of a direct dye solution Lumicrease® Orange 3LG (Colour Index Direct Orange 107) which had been prepared according to the manufacturer's directions. The contents of the beaker were stirred for 45 minutes on an apparatus which continually rotated the beaker at a speed of 60 rpm. Afterwards the textile was removed. The piece of textile was labeled as the "dye exhaustion sample". Using an ACS Model CS5 Chromasensor® spectrophotometer the light reflectance of the textile pieces were measured so to provide a comparison of the relative takeup of the dye in the second laboratory beaker as compared to that of the first laboratory beaker. The "dye exhaustion sample" was determined to have exhausted 84% of the direct dye in the bath. Further, as the conditions of the bath in the second beaker were as close as possible approximation of the conditions in the washing machine, the same dye exhaustion was assumed to have occurred in the washing machine, and the dye exhaustion in the washing machine was assigned a value of 84%.

This test was used to determine the percentage of dye exhaustion as the spectrophotometer could not accurately read the amount of a direct dye absorbed by the denim textile due to the presence of the other dye used to originally dye the denim textile.

Example B

The processes according to Example A were repeated, except that as the direct dye Lumicrease® Yellow 3LG (Colour Index Direct Yellow 98) (available from Sandoz Chemicals Inc.) was used in the place of Lumicrease® Orange 3LG. As in the prior Example, the treated denim was observed to have effectively been overdyed by the Lumicrease® Yellow 3LG. The textile was observed to be uniformly overdyed, providing a color cast to the previously dyed warp yarn and good coloration by the direct dye evident at abrasion points, seams, and in the fill yarn. Evaluation of the dye exhaustion by visual inspection indicated very good dye exhaustion, estimated in excess of 80%.

Example C

The processes according to Example A were repeated, except that as the direct dye Lumicrease® Red Violet 3LB (Colour Index Direct Violet 47) (available from Sandoz Chemicals Inc.) was used in the place of Lumicrease® Orange 3LG. As in the prior Example, the treated denim was observed to have effectively been overdyed by the Lumicrease® Red Violet 3LB. Good exhaustion of the dye was observed. The textile was observed to be uniformly overdyed, providing a color cast to the previously dyed warp yarn and good coloration by the direct dye evident at abrasion points, seams, and in the fill yarn. Evaluation of the dye exhaustion indicated that 80% of the direct dye was exhausted.

Example D

The processes according to Example A were repeated, except that as the direct dye Pyrazol® Fast Turquoise FBL (Colour Index Direct Blue 199) (available from Sandoz Chemicals Inc.) was used in the place of Lumicrease® Orange 3LG. As in the prior Example, the treated denim was observed to have effectively been overdyed by the Pyrazol® Fast Turquoise FBL. Good exhaustion of the dye was observed. The textile was observed to be uniformly overdyed, providing a color cast to the previously dyed warp yarn and good coloration by the direct dye evident at abrasion points, seams, and in the fill yarn. Evaluation of the dye exhaustion indicated that 84% of the direct dye was exhausted.

It will be appreciated that the instant specifications and examples set forth herein are by way of illustration and not limitation, and that various modifications and changes may be made without departing from the spirit and scope of the present invention, whose limitations are bounded only by the appendant claims.

I claim:

1. A single bath process for obtaining a stone washed and overdyed appearance on a dyed denim textile or a dyed denim textile-containing article characterized by:

contacting the denim textile or article with a single aqueous bath containing an effective amount of water soluble or water-dispersible dye suitable for overdying and an effective amount of a cellulase enzyme suitable for stone washing at a pH and temperature at which the cellulase enzyme exhibits stonewashing activity, for a time sufficient to and under conditions suitable for effecting a stone washed and overdyed appearance on said dyed denim textile or dyed denim textile-containing article.

2. The single bath process according to claim 1 wherein the aqueous bath further contains a salt in an amount suitable for aiding the dyeing of the textile or article in an amount suitable for aiding the dyeing of the textile or article.

3. The single bath process according to claim 1 wherein the dye is a direct dye.

4. The single bath process according to claim 3 wherein the aqueous bath is regulated to have a temperature in the range of 30°–40° F. lower than the temperature at which the dye would provide optimal dyeing results without the cellulase being present.

5. The single bath process according to claim 4 wherein the cellulase enzyme exhibits its optimal activity at a pH of 3.8–5.5 and at a temperature of 130°–150° F.

6. The single bath process according to claim 3 wherein the aqueous bath is regulated to have a temperature up to about 160° F.

7. The single bath process according to claim 3 wherein the aqueous bath is regulated to have a temperature in the range of about 130°–160° F.

8. The single bath process according to claim 1 wherein the aqueous bath is regulated to have a pH in the range within which the cellulase enzyme exhibits its optimal activity.

9. The single bath process according to claim 1 wherein the aqueous bath is regulated to have a temperature in the range within which the cellulase enzyme exhibits its optimal activity.

10. The single bath process according to claim 1 wherein the denim textile-containing article is an article of apparel.

11. An aqueous bath composition for imparting a stone washed and overdyed appearance on a denim textile or a denim textile-containing article which comprises:

a water soluble or water-dispersible dye and a cellulase enzyme in amounts effective to impart a stonewashed and overdyed appearance to said denim textile or denim textile-containing article.

12. The aqueous bath composition according to claim 11 in which the dye is a direct dye.

13. The aqueous bath composition according to claim 11 which further comprises a salt in an amount suitable for aiding the dyeing of the textile or article.

14. A textile or a textile-containing article treatment composition which comprises:

a cellulase enzyme, a direct dye and a salt in amounts effective to impart a stonewashed and overdyed appearance to a textile or a textile-containing article wherein the salt is included in an amount in excess of that amount which would provide optimal results at 190°–200° F. with the amount of the direct dye included in the textile treatment composition without the cellulase being present.

* * * * *